(12) United States Patent
Biffi

(10) Patent No.: US 11,464,814 B2
(45) Date of Patent: Oct. 11, 2022

(54) TOPICAL COMPOSITION FOR USE IN THE TREATMENT OF INFLAMMATORY BOWEL DISEASE

(71) Applicant: SOFAR SPA, Trezzano Rosa (IT)

(72) Inventor: Andrea Biffi, Urgnano (IT)

(73) Assignee: SOFAR SPA, Trezzano Rosa (IT)

( * ) Notice: Subject to any disclaimer, the term of this patent is extended or adjusted under 35 U.S.C. 154(b) by 0 days.

(21) Appl. No.: 15/305,470

(22) PCT Filed: Apr. 22, 2015

(86) PCT No.: PCT/IB2015/052938
§ 371 (c)(1),
(2) Date: Oct. 20, 2016

(87) PCT Pub. No.: WO2015/162570
PCT Pub. Date: Oct. 29, 2018

(65) Prior Publication Data
US 2017/0035816 A1 Feb. 9, 2017

(30) Foreign Application Priority Data
Apr. 23, 2014 (IT) .................. MI2014A000751

(51) Int. Cl.
| A61K 35/747 | (2015.01) |
|---|---|
| A61K 9/00 | (2006.01) |
| A61K 31/728 | (2006.01) |
| A61K 47/26 | (2006.01) |
| A61K 47/38 | (2006.01) |
| A61K 47/36 | (2006.01) |
| A61K 9/08 | (2006.01) |
| A61K 45/06 | (2006.01) |

(52) U.S. Cl.
CPC .......... *A61K 35/747* (2013.01); *A61K 9/0031* (2013.01); *A61K 9/08* (2013.01); *A61K 31/728* (2013.01); *A61K 45/06* (2013.01); *A61K 47/26* (2013.01); *A61K 47/36* (2013.01); *A61K 47/38* (2013.01)

(58) Field of Classification Search
CPC ...... A61K 47/36; A61K 47/38; A61K 9/0031; A61K 9/08; A61K 2300/00; A61K 31/728; A61K 35/747; A61K 45/06; A61K 47/26; A61P 1/00; A61P 1/04
See application file for complete search history.

(56) References Cited

U.S. PATENT DOCUMENTS

| 5,531,989 | A | 7/1996 | Paul | |
|---|---|---|---|---|
| 6,770,246 | B1 | 8/2004 | Husek | |
| 7,510,734 | B2 * | 3/2009 | Sullivan | A61K 8/99 424/780 |
| 2002/0090416 | A1 | 7/2002 | Connolly | |
| 2003/0031659 | A1 | 2/2003 | Farmer | |
| 2003/0092163 | A1 | 5/2003 | Collins et al. | |
| 2003/0157146 | A1 | 8/2003 | Rautonen et al. | |
| 2003/0190369 | A1 | 10/2003 | Lovett | |
| 2004/0170617 | A1 | 9/2004 | Finegold | |
| 2005/0196480 | A1 | 9/2005 | Sullivan | |
| 2006/0057704 | A1 | 3/2006 | Schlothauer et al. | |
| 2006/0067921 | A1 | 3/2006 | Conway | |
| 2008/0081035 | A1 | 4/2008 | Parmely et al. | |
| 2008/0193603 | A1 | 8/2008 | Hayes et al. | |
| 2008/0241226 | A1 | 10/2008 | Abeln et al. | |
| 2009/0061446 | A1 | 3/2009 | Niimi et al. | |
| 2009/0098088 | A1 | 4/2009 | Taylor et al. | |
| 2009/0220481 | A1 * | 9/2009 | Maes | A61K 8/645 424/94.61 |
| 2009/0274662 | A1 | 11/2009 | Magowan et al. | |
| 2009/0312282 | A1 * | 12/2009 | Yoshida | A23L 2/52 514/54 |
| 2010/0074994 | A1 | 3/2010 | Harel et al. | |
| 2010/0112564 | A1 | 5/2010 | Zhao et al. | |
| 2011/0014167 | A1 | 1/2011 | Bindels et al. | |
| 2011/0038837 | A1 | 2/2011 | Nishida et al. | |
| 2011/0052538 | A1 | 3/2011 | Brown et al. | |
| 2011/0166100 | A1 | 7/2011 | Wu | |
| 2011/0305744 | A1 * | 12/2011 | Russo | A61K 9/0031 424/430 |
| 2012/0251512 | A1 | 10/2012 | Farmer et al. | |
| 2012/0269865 | A1 | 10/2012 | Roughead et al. | |
| 2012/0301451 | A1 | 11/2012 | Braenning et al. | |
| 2012/0322773 | A1 | 12/2012 | Pravda | |
| 2016/0296569 | A1 | 10/2016 | Guglielmetti et al. | |
| 2016/0348155 | A1 | 12/2016 | Guglielmetti et al. | |
| 2019/0192590 | A1 | 6/2019 | Biffi | |

(Continued)

FOREIGN PATENT DOCUMENTS

| CN | 1161795 A | 10/1997 |
|---|---|---|
| CN | 1701116 A | 11/2005 |

(Continued)

OTHER PUBLICATIONS

Zheng, L. et al. "Regulation of colonic epithelial repair in mice by toll-like receptors and hyaluronic acid," astroenterology 2009: 137: 2041-2051.

Olivia, S. et al., "Randomized clinical trial: the effectiveness of Lactobacillus reuteri ATCC 55730 rectal enema in children with active distal ulcerative colitis," Alimentary Pharmacology & Therapeutics, vol. 35, No. 3, (Dec. 8, 2011), pp. 327-334.

Scaldaferri, F. et al. "Gut microbial flora, prebiotics and probiotics in IBD: their current usage and utility", BioMed Research International (2013), 9 pages.

(Continued)

*Primary Examiner* — Blaine Lankford
(74) *Attorney, Agent, or Firm* — Steinfl + Bruno LLP

(57) ABSTRACT

The present invention relates to a topical composition containing a probiotic and hyaluronic acid or a pharmaceutically acceptable salt thereof, for use in the treatment and/or prevention of inflammatory bowel disease.

26 Claims, No Drawings

(56) References Cited

U.S. PATENT DOCUMENTS

| | | |
|---|---|---|
| 2019/0290706 A1 | 9/2019 | Biffi et al. |
| 2019/0345268 A1 | 11/2019 | Biffi et al. |
| 2021/0186075 A1 | 6/2021 | Biffi et al. |
| 2021/0236565 A1 | 8/2021 | Biffi |

FOREIGN PATENT DOCUMENTS

| | | |
|---|---|---|
| CN | 1840206 A | 10/2006 |
| CN | 101636173 A | 1/2010 |
| CN | 102919922 A | 2/2013 |
| CN | 108743851 A | 11/2018 |
| EP | 1145643 A1 | 10/2001 |
| EP | 2407532 A2 | 1/2012 |
| JP | H0517363 A | 1/1993 |
| JP | 2005508617 A | 4/2005 |
| JP | 2005534315 A | 11/2005 |
| JP | 2010512755 A | 4/2010 |
| JP | 2010161944 A | 7/2010 |
| JP | 2013515051 A | 5/2013 |
| RU | 2182008 | 5/2002 |
| WO | 00/54788 A1 | 9/2000 |
| WO | 03090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2007/140621 A1 | 12/2007 |
| WO | 2008/119012 A2 | 10/2008 |
| WO | 2010/008278 A1 | 1/2010 |
| WO | 2010008272 A1 | 1/2010 |
| WO | 2010/099824 A1 | 9/2010 |
| WO | 2011036539 A1 | 3/2011 |
| WO | 2012154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2015/172191 A1 | 11/2015 |
| WO | 2016/030320 A1 | 3/2016 |
| WO | 2017/195182 A1 | 11/2017 |
| WO | 2017/212433 A1 | 12/2017 |
| WO | 2018/100549 A1 | 6/2018 |
| WO | 2018/109520 A1 | 6/2018 |
| WO | 2018/109730 A1 | 6/2018 |
| WO | 2008/148798 A2 | 12/2018 |
| WO | 2019/019961 A1 | 1/2019 |
| WO | 2019/053604 A1 | 3/2019 |
| WO | 2019/111189 A1 | 6/2019 |
| WO | 2021/053636 A1 | 3/2021 |
| WO | 2021/053639 A1 | 3/2021 |
| WO | 2021/053641 A2 | 3/2021 |
| WO | 2021/053642 A1 | 3/2021 |
| WO | 2021/090228 A1 | 5/2021 |
| WO | 2021/090228 A4 | 7/2021 |

OTHER PUBLICATIONS

Food and Agriculture Organization. Health and nutritional properties of probiotics in food including powder milk with live lactic acid bacteria. (Oct. 2001), 34 pages.

Martin, R. et al. "Role of commensal and probiotic bacteria in human health: a focus on inflammatory bowel disease", Microbial Cell Factories (2013), 12: 71.

Floch, M.H. et al. "Recommendations for probiotic use—2011 Update", J. Clin. Gastroenterol. (2011), 45: S168-S171.

D'Inca, R. et al. "Rectal administration of Lactobacillus Casei DG modifies flora composition and Toll-Like receptor expression in colonic mucosa of patients with mild ulcerative colitis", Dig. Dis. Sci. (2011), 56: 1178-1187.

DeSouza, M.M. et al. "Effects of budesonide and probiotics enemas on the systemic inflammatory response of rats with experimental colitis", Acta Cirúrgica Brasileira (2007), 22 (Suppl. 1): 40-45.

Matthes, H. et al. "Clinical trial: probiotic treatment of acute distal ulcerative colitis with rectally administered *Escherichia coli* Nissle 1917 (EcN)", BMC Complementary and Alternative Medicine (2010), 10: 13.

Orlando, A. et al. "Clinical implications of mucosal healing in the management of patients with inflammatory bowel disease", Digestive and Liver Disease (2013), 45, 986-991.

Mazzouli, S. et al. "Definition and evaluation of mucosal healing in clinical practice", Digestive and Liver Disease (2013), 45, 969-977.

Collins, M.N. and Birkinshaw C. "Hyaluronic acid based scaffolds for tissue engineering—A review", Carbohydrate Polymers (2013), 1262-1279.

Necas, J. et al. "Hyaluronic acid (hyaluronan): A review", Veterinarni Medicina (2008), 53(8): 397-411.

Fakhari, A. and Berkland C. "Applications and emerging trends of hyaluronic acid in tissue engineering, as a dermal filler and in osteoarthritis treatment", Acta Biomaterialia (2013), 9, 7081-7092.

Price, R.D. et al. "Hyaluronic acid: the scientific and clinical evidence", Journal of Plastic, Reconstructive & Aesthetic Surgery (2007), 60: 1110-1119.

Zheng, L. et al. "Regulation of colonic epithelial repair in mice by toll-like receptors and hyaluronic acid," Gastroenterology 2009: 137: 241-2051.

PCT International Search Report and Written Opinion dated Jul. 31, 2016, for Intl. App. No. PCT/IB2015/052938, from which the instant application is based, 9 pgs.

Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Study," United European Gastroenterology Journal: 1(1S) (A219).

Office Action in Corresponding Japanese Patent Application No. 2016-564193, dated Apr. 2, 2019.

Ausubel et al, Current Protocols in molecular biology, edited vols. 1 and 2. John Wiley & Sons, Inc., Media, PA,1994.

Balzaretti et al., "A Novel rhamnose-rich heterp-exopolysaccharide isolated from Lactobacillus paracasei DG activates THP-1 human monocytic cells" *University of Huddersfiled Repository Article for Applied and Environmental Microbiology*.Jan. 17, 2017.

Balzaretti et al., "Exploring Lactobacillus paracasei probiosis and metabolic potential", University of Milan PhD thesis, 2015, pp. 1-132.

Ciucanu I. et al. "A simple and rapid method for the permethylation of carbohydrates" *Carbohydrate Research*,131(1984) pp. 209-217.

Communication pursuant to Article 94(3) EPC for EP Application No. 14790322.3 filed on Sep. 5, 2014 on behalf of SOFAR S.P.A. dated Jan. 31, 2020 8 pages.

Di Mario Francesco et al., "Use of mesalazine in diverticular disease." Journal of Clinical Gastroenterology. vol. 40, Suppl 3, Aug. 2006.

EFSA Journal, "Scientific Opinion on the maintenance of the list of QPS biological agents intentionally added to food and feed (2012 update)1" EFSA Journal2012; 10(12):3020. 84 pages.

European Food Safety Authority EFSA journal (2012) 10(6): 2723.

Evans S. "Clinical trial structures" *J Exp Stroke Transl Med*.Mar. 2011, pp. 1-16, 16 pages.

"Example Cross-Over Study Design {A Phase 11, Randomized, Double-Blind Crossover Study of Hypertena and Placebo in Participants with High Blookd Pressure)". ClinicalTrials.gov (2012).

FAO and WHO et al; "Live microorganisms which, when administered in adequate amounts, confer a health benefit on the host", *World Health Organizations and Food Agriculture Organization*. 2001.

Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.

Ferrario et al J. Nutrition (published online Sep. 3, 2014) 144: 1787-1796 (Year: 2014).

(56) References Cited

OTHER PUBLICATIONS

Final Office Action for U.S. Appl. No. 14/916,959, filed Mar. 4, 2016 on behalf of SOFAR SPA, dated Jul. 23, 2019. 23 pages.
Final Office Action for U.S. Appl. No. 14/916,961, filed Mar. 4, 2016 on behalf of SOFAR S.P.A dated Jan. 2, 2020 16 pages.
Final Office Action for U.S. Appl. No. 14/916,961, filed Mar. 4, 2016 on behalf of SOFAR S.P.A. dated Mar. 13, 2018. 15 pages.
Final Office Action for U.S. Appl. No. 14/916,959, filed Mar. 4, 2016 on behalf of SOFAR SPA, dated Apr. 20, 2018. 26 pages.
Gerwig G. et al., "Determination of the absolute configuration of mono-saccharides in complex carbohydrates by capillary G.L.C." *Carbohydrate Research*,77(1979) pp. 1-7.
Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75" *Applied and Environmental Microbiology*,vol. 80, No. 17,Sep. 2014 pp. 5161-5169.
Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, pp. 1123-1132. 2011.
International Search Report for International Application No. PCT/IB2014/064284 filed on Sep. 5, 2014 on behalf of SOFAR SPA, dated Jan. 26, 2015. 6 pages.
International Search Report for International Application No. PCT/IB2014/064285 filed on Sep. 5, 2014 on behalf of SOFAR SPA, dated Jan. 29, 2015. 4 pages.
International Search Report for International Application No. PCT/IB2017/052850 filed on May 15, 2017 on behalf of SOFAR SPA, dated Aug. 17, 2017. 4 pages.
International Search Report for International Application No. PCT/IB2017/053389 filed on Jun. 8, 2017 on behalf of SOFAR SPA, dated Oct. 6, 2017. 5 pages.
International Search Report for International Application No. PCT/IB2017/057576 filed on Dec. 1, 2017 on behalf of SOFAR SPA, dated Feb. 22, 2018. 5 pages.
International Search Report for International Application No. PCT/IB2017/057980 filed on Dec. 15, 2017 on behalf of SOFAR SPA, dated Mar. 19, 2018. 4 pages.
Italia il Ministero della Salute (*Linee Guida su Probiotici e Prebiotici rev.*May 2013).
Jacobsen et al., "Screening of Probiotic Activities of Forty-Seven Strains of *Lactobacillus* spp. By In Vitro techniques and Evaluation of the Colonization Ability of Five Selected Strains in Humans" Applied and Environmental Microbiology, Nov. 1999, p. 4949-4956. 8 pages.
Larsen et al., "Predominant genera of fecal microbiota in children with atopic dermatitis are not altered by intake of probiolic bacteria *Lactobacillus acidophilus* NCFM and *Bifidobacterium animalis* subsp. *lacis* Bi-07," FEMS Microbiol Ecol 75: 482-496 (2011).
Laws et al., "Biosynthesis, characterization, and design of bacterial exopolysacharides from lactic acid bacteria",*Biotechnology Advances*. vol. 19,2001. pp. 597-625.
LeBlanc et al., "Beneficial effects on host energy metabolism of shot-chain fatty acids and vitamins produced by commensal and probiotic bacteria," Microbial Cell Factories 16:79: 1-10 (2017).
Lombardo L; et al "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of *Lactobacillus paracasei* Subsp.*paracasei* F19 with Gluco-Oligosaccharides in the Short-term Treatment of Irritable Bowel Syndrome" Microbial Ecology in Health and Disease 21: 28-32 (2009).
Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3: 1-7).

Milani et al., Assessing the fecal microbiota: and optimized ion torrent 16S rRNA gene-based analysis protocol. PLoS One. 2013; 8(7); e68739, 12 pages. Published2013.
Montalto M. et al., "Clinical trial: the effects of a probiotic mixture on non-steroidal anti-inflammatory drug enteropathy—a randomized, double-blind, cross-over, placebo-controlled study" *Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59:595-700(1993).
Neiwert et al., "Structural Investigation of rhamnose-rich polysaccharides from *Streptococcus dysgalactiae* bovine mastitis isolate" Carbohydrate Research, vol. 389,2014. pp. 192-195.
Non-Final Office Action for U.S. Appl. No. 14/916,961, filed Mar. 4, 2016 on behalf of SOFAR S.P.A. dated Jun. 30, 2017. 21 pages.
Non-Final Office Action for U.S. Appl. No. 14/916,961, filed Mar. 4, 2016 on behalf of SOFAR S.P.A. dated Jul. 25, 2019. 18 pages.
Non-Final Office Action for U.S. Appl. No. 14/916,959, filed Mar. 4, 2016 on behalf of SOFAR S.P.A. dated Mar. 13, 2020 25 pages.
Non-Final Office Action for U.S. Appl. No. 14/916,959, filed Mar. 4, 2016 on behalf of SOFAR SPA, dated Aug. 31, 2017. 27 pages.
Non-Final Office Action for U.S. Appl. No. 14/916,959, filed Mar. 4, 2016 on behalf of SOFAR SPA, dated Nov. 19, 2018. 15 pages.
Office Action in corresponding Chinese Patent Application No. 201480049296.4, dated Aug. 27, 2019.
Okuda et al., "Virtual metagenome reconstruction from 16S rRNA gene sequences".*Nature Communications*,2012. 8 pages.
Olveira et al; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Plant et al., "Association of *Laclobacillus* spp. with Peyer's Patches in Mice", Clinical and Diagnostic Laboratory Immunology 8: 320-324 (2001).
Polak-Berecka et al., "Physiocochemical characterization of exopolysaccharides produced by lactobacillus rhamnosus on various carbon sources", Carbohydrate Polymers, vol. 117, 2015. pp. 501-509.
Restriction Requirement for U.S. Appl. No. 14/916,961, filed Mar. 4, 2016 on behalf of SOFAR S.P.A. dated May 10, 2019. 7 pages.
Sambrook et al. Molecular cloning: A Laboratory Manual. 3rd ed., vols. 1,2 and 3 cold Spring Harbor Laboratory Press,2001, 2100 pp.
Sanlibaba et al., "Exopolysaccharides production by lactic acid bacteria",*Applied Microbiology*, vol. 2,May 20, 2016.
Sasaki M.. et al., "Transglucosidase improves the gut microbiota profile of type 2 diabetes mellitus patients: a randomized double-blind, placebo-controlled study" *BMC Gastroenterology*, 13:81,2013.
Savino et al., "Lactobacillus reuteri DSM 17938 in Infantile Colic: A Randomized, Double-Blind, Placebo-Controlled Trial", Pediatrics 126: e526-e533 (2010).
Siew Chien NG et al., "Effect of probiotic bacteria on the intenstinal microbiota in irritable bowel syndrome" Journal of gastroenterology and hepatology.2013.
Spiller et al., "Randomized double blind placebo-controlled trial of *Saccharomyces cerevisiae* CNCM I-3856 in irritable bowel syndrome: improvement in abdominal pain and bloating in those with predominant constipation" *United European Gastroenterology Journal.* 2016.
Stuknyte M. et al., "Potential immunomodulatory activity of bovine casein hydrolysates produced after digestion with proteinases of lactic acid bacteria" *International Dairy Journal*, 21(2011) pp. 763-769.
Taverniti and Gugliemetti et al., "The immunomodulatory properties of probiotic microorganisms beyond their viability (ghost probiotics: proposal of paraprobiotic concept)" Department of Food Science and Microbiolgy (DiSTAM), , 6:261-274(2011).
Turnbaugh et al., "The Effect of Diel on the Human Gut Microbiome: A Metagenomic Analysis in Humanized gnolobiotic Mice," Sci Transl Med: (2009).
Tursi et al., "Balsalazide and/or high-potency probiotic mixture (VSL#3) in maintaining remission after attack of acute, uncomplicated diverticulitis of the colon", International Journal of Colorectal

(56) References Cited

OTHER PUBLICATIONS

Disease; Clinical and Molecular Gastroenterology an Surgery, Sprinfer, Berlin, DE. vol. 22, No. 9,Mar. 28, 2007. pp. 1103-1108.
Tursi et al., "Effect of Lactobacillus casei supplementation on the effectiveness and tolerability of a new second-line 10-day quadruple therapy after failure of a first attempt to cure Helicobacter pylori infection," Med Sci Monit 10: CR662-666 (2004).
Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.
Tursi et al., "Mesalazine and/or Lactobacillus casei in preventing recurrence of symptomatic uncomplicated diverticular disease of the colon: A Prospective , randomized, open-label study", Journal of Clinical Gastroenterol, Raven Press LTD, NY, New York. vol. 40, No. 2, Apr. 1, 2006. pp. 312-316.
Tursi et al., "Randomised clinical trial: mesalazine and/or probiotics in maintaining remission of symptomatic uncomplicated diverticula disease—double-blind, randomized, placebo-controlled study" Alimentary Pharmacology & Therapeutics. vol. 38, No. 7.Oct. 19, 2013. pp. 741-751.
U.S. National Library of Medicine, "Effect of Lactobacillus Casei DG (Enterolactis Plus) in Patient with irritable Bowel Syndrome: a Pilot Study", ClinicalTriaals.gov,Feb. 11, 2015.
U.S. National Library of Medicine Efficacy Evaluation of a Commercial Preparation Containing Lactobacillus Casei DG on the Reduction of the Painful Symptoms Related to the Irritable Bowel Syndrome (IBS).*A Pilot Clinical Study*.Feb. 28, 2014.
Valerio et al., "Effects of Probiotic Lactobacillus paracasei-enriched Artichokes on Constipated Patients", J Clin Gastroenterol,Sep. 10, 2010.
Vernia et al. Dig. Disease Sci. (1988) 33(11): 1353-135 (Year: 1988).
Vinogradov et al., "Structural studies of the rhamnoseirch cell wall polysaccharide of lactobacillus casei BL23" *Carbohydrate Research* vol. 435,Oct. 8, 2016. pp. 156-161.
"Why VSL#3" (Obtained from https://vsl3.com/hcp/vsl-info on Aug. 22, 2017 , 4 pages.
Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).
Written Opinion for International Application No. PCT/IB2014/064284 filed on Sep. 5, 2014 on behalf of SOFAR SPA, dated Jan. 26, 2015. 7 pages.
Written Opinion for International Application No. PCT/IB2014/064285 filed on Sep. 5, 2014 on behalf of SOFAR SPA, dated Jan. 29, 2015. 7 pages.
Written Opinion for International Application No. PCT/IB2017/052850 filed on May 15, 2017 on behalf of SOFAR SPA, dated Aug. 17, 2017. 6 pages.
Written Opinion for International Application No. PCT/IB2017/053389 filed on Jun. 8, 2017 on behalf of SOFAR SPA, dated Oct. 6, 2017. 7 pages.
Written Opinion for International Application No. PCT/IB2017/057576 filed on Dec. 1, 2017 on behalf of SOFAR SPA, dated Feb. 22, 2018. 8 pages.
Written Opinion for International Application No. PCT/IB2017/057980 filed on Dec. 15, 2017 on behalf of SOFAR SPA, dated Mar. 19, 2018. 8 pages.
Written Opinion for International Application PCT/IB2015/052938 filed on Apr. 22, 2015 on behalf of SOFAR SPA, dated Jul. 31, 2015. 5 pages.
Zhang et al., "Isolated exopolysaccharides from lactobacillus rhamnosus GG alleviated adipogenesis mediated by TLR2 in mice" *Scientific reports*. vol. 6,Oct. 27, 2016.
Non-Final Office Action for U.S. Appl. No. 16/301,361, filed Nov. 13, 2018 on behalf of SOFAR S.P.A. dated May 8, 2020. 20 pages.
Havea, Palatasa, Protein interactions in milk protein concentrate powders, Int'l Dairy Journal 16 (2006) 415-422.
Balzaretti S. et al., "A novel hetero-exopolysaccharide mediates the recognition of Lactobacillius paracasei DG by the immune system" Pharmabiotics Conference2015, Paris, Oct. 29-30, 2015,1 page.
Bienenstock J et al., "New insights into probiotic mechanisms" *Gut Microbes*, vol. 4 Issue 2,Apr. 2013, 7 pages.
Canadian Examination Search Report for CA Application No. 2,923,390 filed on Sep. 5, 2014 on behalf of SOFAR S.P.A. dated Jan. 26, 2021 4 pages.
Colombian Office Action for CO Application No. NC2018/0010954 filed on Nov. 1, 2018 on behalf of SOFAR S.P.A. dated Feb. 5, 2021 9 pages. (Partial English + Original).
Colombian Office Action for CO Application No. NC2019/0007116 filed on Jul. 2, 2019 on behalf of SOFAR S.P.A. dated Jan. 15, 2021 19 pages. (English + Original).
Declaration for the self-archiving of the doctoral thesis for "Exploring Lactobacillius Paracasei Probiosis and Metabolic Potential" by Balzaretti, Silvia Dated: Nov. 20, 2015 5 pages (English + Original).
Laws A. et al., "Determination of the structure and molecular weights of the exopolysaccharide produced by Lactobacillus acidophilus 5e2 when grown on different carbon feeds." *Carbohydr Res*.Feb. 4, 2008;343(2):301-7.
Notice of Allowance for U.S. Appl. No. 16/301,361, filed Nov. 13, 2018 on behalf of SOFAR S.P.A. dated Feb. 1, 2021 8 pages.
Paoluzi O.A., et al al. "Low efficacy of levofloxacin-doxycycline-based third-line tripletherapy for Helicobacter pylori eradication in Italy." *World Journal of Gastroenterology*21: 6698-705,Jun. 2015.
Rosania R. et al. "Effect of probiotic or prebiotic supplementation on antibiotic therapy in the small intestinal bacterial overgrowth: a comparative evaluation." Curr Clin Pharmacol . May 2013;8(2):169-72. 5 pages.
Mexican Office Action for MX Application No. MX/a/2016/002766 filed on Sep. 5, 2014 on behalf of SOFAR S.P.A. dated Mar. 18, 2021 10 pages (English + Original).
Screenshot from the web-archive of the Milano University, Nov. 23, 2015, 2 pages. (English + Original).
Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.
Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.
Australian Examination Report for AU Application No. 2017263294 filed on May 15, 2017 on behalf of SOFAR S.P.A. dated Oct. 30, 2020 5 pages.
Balzaretti S. et al., "The vaginal isolate Lactobacillus paracasei LPC-S01 (DSM 26760) is suitable for oral administration" *Frontiers in Microbiology*, vol. 6, art. 952,Sep. 2015 , 13 pages.
Banasiewicz T. et al., "Determination of butyric acid dosage based on clinical and experimental studies—a literature review" *Gastroenterology Review*,2020, pp. 119-125.
Borren N. et al., "Alterations in Fecal Microbiomes and Serum Metabolomes of Fatigues Patients With Quiescent Inflammatory Bowel Diseases" *Clinical Gastroenterology and Hepatology*,Mar. 2020, 35 pages.
Canadian Office Action for CA Application No. 2,923,392 filed on Sep. 5, 2014 on behalf of SOFAR S.P.A. dated Jun. 1, 2020 4 pages.
Cassard L. et al, "Individual strains of Lactobacillus paracasei differentially inhibit human basophil and mouse mast cell activation," Immunity, Inflammation, and Disease vol. 4, Issue 3., 2016. 11 Pages.
Chassard C. et al., "Functional dysbiosis within the gut microbiota of patients with constipated-irritable bowel syndrome" *Alimentary Pharmacology and Therapeutics*, 2012, pp. 828-838.
Chilean Office Action for CL Application No. 201803193 filed on Sep. 5, 2014 dated Apr. 16, 2020 16 pages. (English + Original).
Chinese Decision of Rejection for CN Application No. 201480049296.4 filed on Sep. 5, 2014 on behalf of SOFAR S.P.A. dated Dec. 9, 2020 (English + Original) 12 pages.
Chinese Office Action for CN Application No. 201480049288 filed on Sep. 5, 2014 on behalf of SOFAR S.P.A. dated Sep. 16, 2020 8 pages. (English + Original).

(56) References Cited

OTHER PUBLICATIONS

Colombian Office Action for CO Application No. NC2018/0010950 filed on Sep. 5, 2014 on behalf of SOFAR S.P.A. dated Jul. 27, 2020 11 pages. (Partial English + Original).
Compare D. et al., "Lactobacillus casei DG and its postbiotic reduce the inflammatory mucosal response: an ex-vivo organ culture model of post-infectious irritable bowel syndrome" *BMC Gastroenterology*,2017, 8 pages.
Costalos et al., "Enteral feeding of premature infants with *Saccharomyces boulardii*" *Early Human Development*, 74,(2003), 89-96.
Cremon C. et al., "Effect of Lactobacillus paracasei CNCM I-1572 on symptoms, gut microbiota, short chain fatty acids, and immune activation in patients with irritable bowel syndrome: A pilot randomized clinical trial" *UEG Journal*,Sep. 2017, 10 pages.
Crohn's and Colitis Foundation of America. Inflammatory Bowel Disease and Inflammatory Bowel Syndrome: Similarities and Differences. 2014. 12 Pages.
Cui Y. et al., "Revolution of Chronic Diarrhoea" China Medicine, Science, and Technology Publishing House, 1st edition, Jan. 2013, pp. 19-23 (Original + Partial Google Translation).
Eurasian Notification of Grant for Application No. 201690464/28 filed on Sep. 5, 2014 on behalf of SOFAR S.P.A. dated Jun. 9, 2020 2 pages. (English + Original).
Final Office Action for U.S. Appl. No. 14/916,959, filed Mar. 4, 2016 on behalf of SOFAR S.P.A. dated Aug. 21, 2020 48 pages.
Final Office Action for U.S. Appl. No. 16/301,361, filed Nov. 13, 2018 on behalf of SOFAR S.P.A. dated Sep. 21, 2020 11 pages.
Gargari G. et al., "Fecal Clostridiales distribution and short-chain fatty acids reflect bowel habits in irritable bowel syndrome" Environmental Microbiology, Sep. 2018, 31 pages.
Guo, Y., et al., "Irritable Bowel Syndrome is Positively Related to Metabolic Syndrome: A Population-Based Cross-Sectional Study," PLoS One. 9(11): e112289. Nov. 10, 2014. 6 pages.
Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.
Irritable Bowel Syndrome—Wikipedia, dated Sep. 16, 2020. 33 pages, https://en.wikipedia.org/wiki/Irritable_bowel_syndrome.
Israeli Office Action for Application No. 244391 filed on Mar. 2, 2016 on behalf of SOFAR S.P.A. dated Jun. 24, 2020 4 pages. (English + Original).
Israeli Office Action for Application No. 269107 filed on Sep. 3, 2019 on behalf of SOFAR S.P.A. dated May 17, 2020 5 pages (English + Original).
Israeli Office Action for IL Application No. 244391 filed on behalf of SOFAR S.P.A. dated Oct. 27, 2020 (English + Original) 4 pages.
Japanese Office Action for JP Application No. 2016564193 filed on Apr. 22, 2015 on behalf of SOFAR S.P.A. dated Feb. 18, 2020 11 pages (English + Original).
Kay, RM., et al., "Dietary Fiber," J. of Lipid Research, v. 23, 1982. 221-242, 22 Pages.
Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.
Intermountain Healthcare. 2015. Irritable Bowel Syndrome (IBS). Retrieved from: https://intermountainhealthcare.org/services/gastroenterology/conditions/irritable-bowel-syndrome/. 2015. 3 pages.
Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.
Mcfarland, et al., "Strain-Specificity and Disease-Specificity of Probiotic Efficacy: A Systematic Review and Meta-Analysis," Frontiers in Medicine, May 7, 2018. 14 Pages.
Mexican Office Action for MX Application No. MX/a/2016/002766 filed on Sep. 5, 2014 on behalf of SOFAR S.P.A. dated Aug. 13, 2020 10 pages (English + Original).

Non-Final Office Action for U.S. Appl. No. 16/308,330, filed Dec. 7, 2018 on behalf of SOFAR S.P.A., dated May 14, 2020. 23 Pages.
Non-Final Office Action for U.S. Appl. No. 14/916,961, filed Mar. 4, 2016, on behalf of SOFAR S.P.A. dated Jan. 7, 2021. 22 Pages.
Pituch A. et al., "Butyric acid in functional constipation" *Przeglad Gastroenterologiczny*,2013, 4 pages.
Pozuelo M. et al., "Reduction of butyrate and methane producing microorganisms in patients with Irritable Bowel Syndrome" *Nature Scientific Reports*,Apr. 2015, 12 pages.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Restriction Requirement for U.S. Appl. No. 16/465,237, filed May 30, 2019 on behalf of SOFAR S.P.A. dated Dec. 21, 2020 8 pages.
Ringel-Kulka T. et al., "Short Chain Fatty Acids and Intestinal Transit in Patients With Irritable Bowel Syndrome and Healthy Controls" *AGA Abstracts*,May 2012, 1 page.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with mixed refractory constipation" Association of Coloproctology of Great Britain and Ireland, Feb. 2016, 8 pages.
Smokvina T. et al "Lactobacillus paracasei Comparative Genomics: Towards Species Pan-Genome Definition and Exploitation of Diversity," PLOS One, Jul. 19, 2013. 16 Pages.
Sun Q. et al., "Alterations in fecal short-chain fatty acids in patients with irritable bowel syndrome" *Systematic Review and Meta-Analysis*,Jan. 2019, 12 pages.
Third Chinese Office Action for CN Application No. 201480049296.4 filed on Sep. 5, 2014 on behalf of SOFAR S.P.A. dated Mar. 18, 2020 13 pages (English + Original).
Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.
Turco F. et al., "Enteroglial-derived S100B protein integrates bacteria-induced Toll-like receptor signalling in human enteric glial cells" GUT Neurogastroenterology, vol. 63, Mar. 2014, Originally Published online Jan. 3, 2013, 12 pages.
Tursi A. et al., "Assessment of Fecal Microbiota and Fecal Metabolome in Symptomatic Uncomplicated Diverticular Disease of the Colon" *J. Clin Gastroenterol*,Oct. 2016, 4 pages.
Tursi A. et al., "Fecal Microbiota, Fecal and Urinary Metabolic Profiling and Symptomatic Uncomplicated Diverticular Disease of the Colon" *Digestive and Liver Disease*, 2017, 1 page.
Tursi A. et al., "Natural History of Symptomatic Uncomplicated Diverticular Disease: A 13-Year Prospective Study" *AGA Abstracts*,Apr. 2017, 1 page.
Wang Y. et al., "Emerging Infectious Diseases" Science and Technology Documents Publishing House, 1st edition, Jan. 2006, pp. 310-312 (Original + Partial Google Translation).
Watanabe I. et al., "KT-11" *Food Style 21*, vol. 17, No. 6, pp. 62-64,2013. 5 pages (Machine Translation + Original).
Zhuang M. et al., "Abundance of probiotics and butyrate-production microbiome manages constipation via short-chain fatty acids production and hormones secretion" Molecular Nutrition & Food Research, Jul. 2019, 41 pages.
Zhuang M. et al., "Systematic Review and Meta-analysis: Short-Chain Fatty Acid Characterization in Patients With Inflammatory Bowel Disease" *Inflammatory Bowel Disease*, Nov. 2019, 13 pages.
Brussow H. "Problems with the concept of gut microbiota dysbiosis" Microbial Biotechnology, vol. 13(2), 2020, pp. 423-434.
Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.
Non-Final Office Action for U.S. Appl. No. 14/916,959, filed Mar. 4, 2016 on behalf of SOFAR S.P.A. dated Apr. 13, 2021 33 pages.
Non-Final OfficeAction for U.S. Appl. No. 16/308,330, filed Dec. 7, 2018 on behalf ofSOFAR S.P.A. dated Apr. 30, 2021. 38 Pages.

(56) References Cited

OTHER PUBLICATIONS

Notice of Allowance for U.S. Appl. No. 16/301,361, filed Nov. 13, 2018 on behalf of SOFAR S.P.A. dated May 3, 2021 9 pages.
Tuohy K.M. et al., "Survivability of a probiotic Lactobacillus casei in the gastrointestinal tract of healthy human volunteers and its impact on the faecal microflora" *Journal of Applied Mircrobiology*,2007, pp. 1026-1032.
Communication pursuant to Article 94(3) EPC for EP Application No. 14790322.3 filed on Sep. 5, 2014 on behalf of SOFAR S.P.A. dated Jan. 11, 2021, 3 pages.
Canadian Office Action for CA Application No. 2,923,392 filed Sep. 5, 2014 on behalf of Sofar S.P.A. dated Apr. 1, 2021 4 pages.
Canani R. B. et al., "Potential beneficial effects of butyrate in intestinal and extraintestinal diseases" World Journal of Gastroenterology, vol. 17 No. 12, Mar. 2011, 10 pages.
Chooi E. et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" *Healthline*, Sep. 2018, 5 pages.
Colombian Office Action for CO Application No. NC2018/0010950 filed May 15, 2017 on behalf of Sofar S.P.A. dated May 3, 2021 9 pages (English + Original).
Colombian Office Action for Colombian Application No. NC2019/0006257 filed Dec. 15, 2017 on behalf of Sofar S.P.A. dated May 13, 2021 3 pages (English + Original).
De Backer A. I. et al., "Intestinal stenosis from mesenteric injury after blunt abdominal trauma" Eur. Radiol., 1999, pp. 1429-1431.
Gould M. et al., "Diabetic diarrhea" Current Gastroenterology Report, 2009, pp. 354-359 (Abstract only).
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
Laval G. et al., "The use of steroids in the management of inoperable intestinal obstruction in terminal cancer patients: do they remove the obstruction?" Palliative Medicine, 2000, pp. 3-10.
Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 16/465,237, filed May 30, 2019, on behalf of Sofar S.P.A. dated Jul. 9, 2021. 37 Pages.
Notice of Allowance for U.S. Appl. No. 16/301,361, filed Nov. 13, 2018, on behalf of Sofar S.P.A. dated Aug. 4, 2021. 11 Pages.
Restriction Requirement for U.S. Appl. No. 16/467,797, filed Jun. 7, 2019 on behalf of Sofar S.P.A. dated Jun. 15, 2021 6 pages.
Rodriguez-Castro K. I. et al., "Clinical manifestations of chronic atrophic gastritis" Acta Biomed, vol. 89, 2018, pp. 88-92.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Wells D. "Gastritis Diet: What to Eat and What to Avoid" Healthline, Jul. 2020, 11 pages.
Zhang, Z., et al., "Isolated exopolysaccharides from *Lactobacillus rhamnosus* GG alleviated adipogenesis mediated by TLR2 in mice," *Sci Rep* 6, 36083, Oct. 27, 2016. 13 Pages, https://doi.org/10.1038/srep36083.
Australian Examination Report for AU Application No. 2017367302 filed Dec. 1, 2017 on behalf of Sofar S.P.A. dated Jul. 23, 2021 4 pages.
Bacteriotherapy—Merriam-Webster Medical Dictionary, Archive Date: Apr. 26, 2016, 6 pages.
Bassi R. "Mesalazine + *Lactobacillus paracasei* CNCMI1572 vs Mesalazine alone in preventing recurrence of symptom of diverticular disease: a prospective, randomize, open-label study." Colorectal Disease, 2019 1 pages.

Bassi R. "Preventing recurrence of symptomatic diverticular disease of the colon: mesalazine with or without Lactobacillus case DG: a prospective randomized, open label study." European Society of Coloproctology, 2015, 1 page.
Capsule (Pharmacy)—Wikipedia, the free encyclopedia, Archive Date: Apr. 10, 2016, 4 pages.
Chilean Office Action for CL Application No. 201901493 filed Dec. 1, 2017 on behalf of Sofar S.P.A. dated May 6, 2021 24 pages (English + Original).
Chinese Office Action for CN Application No. 201480049288X filed Sep. 5, 2014 on behalf of Sofar S.P.A. dated Aug. 12, 2021 (English + Original) 15 pages.
Colombian Office Action for CO Application No. NC2018/0010954 filed Jun. 2, 2019 on behalf of Sofar S.P.A. dated Jun. 30, 2021 8 pages (Partial English + Original).
Communication pursuant to Article 94(3) EPC for EP Application No. 17817173.2 filed Dec. 1, 2017 on behalf of Sofar S.P.A. dated Sep. 29, 2021 6 pages.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: Mar. 31, 2014 https://web.archive.org/web/20140331225522/http://en.wikipedia.org/wiki/Dysbiosis , 4 pages.
Eurasian Office Action for EA Application No. 202090097/28 filed Sep. 5, 2014 on behalf of Sofar S.P.A. dated Aug. 16, 2021 (English + Original) 10 pages.
Ferrario, et al., "Modulation of Fecal Clostridiales Bacteria and Butyrate by Probiotic Intervention with *Lactobacillus paracasei* DG Varies among Healthy Adults1-3" J. Nutritional Epidemiology, 144. Sep. 3, 2014. pp. 1787-1796. 10 Pages.
Final Office Action for U.S. Appl. No. 14/916,961, filed Mar. 4, 2016, on behalf of Sofar S.P.A. dated Oct. 14, 2021. 26 Pages.
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" *American Journal of Clinical Nutrition*, vol. 23 No. 11, Nov. 1970, pp. 1433-1439.
Iebba V. et al., "Eubiosis and Dysbiosis: the two sides of the microbiota" *New Microbiologica*, vol. 39, 2016, pp. 1-12.
John Hopkins Medicine—Fecal Transplantation (Bacteriotherapy), John Hopkins Division of Gastroenterology and Hepatology, Archive Date: Apr. 2016, 2 pages.
Leonel, A.J., et al. "Butyrate: implications for intestinal function," Current Opinion in Clinical Nutrition and Metabolic Care 15(5): 474-479. 2012. 6 Pages.
Restriction Requirement for U.S. Appl. No. 17/090,669 filed Nov. 5, 2020, on behalf of Sofar S.P.A. dated Sep. 3, 2021. 7 Pages.
Tsimmerman Y. S. "Eubiosis and Dysbiosis of Gastrointestinal Tract: Myths and Reality" *Perm State Medical Academy*, 2013, 27 pages.
World Gastroenterology Organisation Global Guidelines "Probiotics and prebiotics" Feb. 2017, 35 pages.
Allowance of the Brazilian patent application BR 11 2016 005059 2 published in the Official Bulletin n°2651 of Oct. 26, 2021 (Portuguese Only).
Colombian Office Action for CO Application No. NC2019/0007116 filed Jul. 2, 2019 on behalf of Sofar S.P.A. dated Sep. 29, 2021 12 pages (English + Original).
Non-Final Office Action for U.S. Appl. No. 16/467,797, filed Jun. 6, 2019 on behalf of Sofar S.P.A. dated Dec. 14, 2021 35 pages.
Canadian Office Action for CA Application No. 2,923,390 filed Sep. 5, 2014 on behalf of Sofar S.P.A. dated Nov. 29, 2021 5 pages.
Chinese Office Action for CN Application No. 201780029401.1 filed May 15, 2017 on behalf of Sofar S.P.A. dated Dec. 15, 2021 (English + Original) 24 pages.
Colombian Office Action for CO Application No. NC2018/0010950 filed May 15, 2017 on behalf of Sofar S.P.A. dated Oct. 14, 2021 (Partial English + Original) 9 pages.
Final Office Action for U.S. Appl. No. 14/916,959, filed Mar. 4, 2016 on behalf of Sofar S.P.A. dated Dec. 29, 2021. 29 Pages.

(56) References Cited

OTHER PUBLICATIONS

Mexican Office Action for MX Application No. MX/a/2016/022766 filed Sep. 5, 2014 on behalf of Sofar S.P.A. dated Oct. 26, 2021 (Partial English + Original) 12 pages.
Salvetti E. et al., "The Genus Lactobacillus: A Taxonomic Update" *Probiotics & Antimicro. Prot.*, Nov. 2012, vol. 4, pp. 217-226.
Yuanning S. et al., "Analysis of Lactic Acid Bacteria Protein Dissolution and Aroma Production Ability" Chinese Brew, vol. 33 No. 3, Dec. 31, 2014 (English Abstract + Original) 4 pages.
Final Office Action for U.S. Appl. No. 16/308,330, filed Dec. 7, 2018, on behalf of Sofar S.P.A. dated Feb. 9, 2022. 22 Pages.
Patel, R., et a., "New Approaches for Bacteriotherapy: Prebiotics, New-Generation Probiotics, and Synbiotics," *Clinical Infectious Diseases*, vol. 60, Issue supplement 2, May 15, 2015. pp. S108-S121. 15 Pages, https://doi.org/10.1093/cid/civ177.
Cremon C. et al., "Effect of *Lactobacillus paracasei* CNCM 1-1572 on symptoms, gut microbiota, short chain fatty acids, and immune activation in patients with irritable bowel syndrome: A pilot randomized clinical trial" UEG Journal, Sep. 2017, 10 pages.
International Preliminary Report on Patentability for International Application No. PCT/IB2020/060412 filed Nov. 5, 2020 on behalf of Sofar S.P.A. dated May 10, 2022 7 pages.
International Search Report and Written Opinion for International Application No. PCT/IB2020/060412 filed Nov. 5, 2020 on behalf of Sofar S.P.A. dated Mar. 4, 2021 10 pages.
Azad M.D.A.K et al., "Immunomodulatory Effects of Probiotics on Cytokine Profiles" Biomed Research International, vol. 2018, Oct. 2018, pp. 1-10.
Bedford A. et al., "Implications of butyrate and its derivatives for gut health and animal production" *Animal Nutrition*, vol. 4, 2018, pp. 151-159.
Borycka-Kiciak K. et al., "Butyric acid—a well-known molecule revisited" *Gastroenterology Rev*, vol. 12 No. 2, 2017, pp. 83-89.
Cheng A. et al., "Polyphenols from blueberries modulate inflammation cytokines in LPS-induced RAW264.7 macrophages", *Acta. Paediatrica. Supplement, Elsevier*, vol. 69, Jun. 2014, pp. 382-387.
Connors J. et al., "The Role of Succinate in the Regulation of Intestinal Inflammation" *Nutrients*, vol. 11 No. 25, 2019, 12 pages.
Cui J. et al., "NMR-based metabonomics and correlation analysis reveal potential biomarkers associated with chronic atrophic gastritis" *Journal of Pharmaceutical and Biomedical Analysis*, vol. 132, 2017, pp. 77-86.
Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.
Franco V. "Effectiveness of an association of a cranberry dry extract, D-mannose, and the two microorganisms *Lactobacillus plantarum* LP01 and *Lactobacillus paracasei* LPC09 in women affected by cystitis: a pilot study." *US National Library of Medicine*, Nov. 2014, 6 pages.
Gwiazdowska D. et al., "The impact of polyphenols on Bifidobacterium growth", Acta Biochimica Polonica, vol. 62 No. 4, Jan. 2015, 8 pages.
Hajjar R. et al., "The role of butyrate in surgical and oncological outcomes in colorectal cancer" *American Journal of Physiology*, vol. 320, Jan. 2021, pp. G601-G608.
Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.
Hurst N.R. et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.
International Preliminary Report on Patentability for International Application No. PCT/IB2020/058774 filed Sep. 21, 2020 on behalf of Sofar S.P.A. dated Mar. 15, 2022 6 pages.
International Preliminary Report on Patentability for International Application No. PCT/IB2020/058769 filed Sep. 21, 2020 on behalf of Sofar S.P.A. dated Mar. 15, 2022 6 pages.
International Preliminary Report on Patentability for International Application No. PCT/IB2020/058777 filed Sep. 21, 2020 on behalf of Sofar S.P.A. dated Mar. 15, 2022 6 pages.
International Preliminary Report on Patentability for International Application No. PCT/IB2020/058778 filed Sep. 21, 2020 on behalf of Sofar S.P.A. dated Mar. 15, 2022 6 pages.
International Search Report and Written Opinion for International Application No. PCT/IB2020/058778 filed Sep. 21, 2020 on behalf of Sofar S.P.A. dated Feb. 18, 2021 8 pages.
International Search Report and Written Opinion for International Application No. PCT/IB2020/058769 filed Sep. 21, 2020 on behalf of Sofar S.P.A. dated Feb. 18, 2021 8 pages.
International Search Report and Written Opinion for International Application No. PCT/IB2020/058774 filed Sep. 21, 2020 on behalf of Sofar S.P.A. dated Dec. 8, 2020 8 pages.
International Search Report and Written Opinion for International Application No. PCT/IB2020/058777 filed Sep. 21, 2020 on behalf of Sofar S.P.A. dated Apr. 20, 2021 26 pages.
Koradia P. et al., "Probiotic and cranberry supplementation for preventing recurrent uncomplicated urinary tract infections in premenopausal women: a controlled pilot study" *Expert Review of Anti-Infective Therapy*, vol. 17 No. 9, Sep. 2019, pp. 733-740.
Krokowicz L. et al., "Sodium butyrate and short chain fatty acids in prevention of travellers, diarrhoea—a randomized prospective study" *Travel Medicine and Infectious Disease*, Aug. 2013, 17 pages.
Lacombe A. et al., "The potential of berries to serve as selective inhibitors of pathogens and promoters of beneficial microorganisms" *Food Quality and Safety*, vol. 1 No. 1, Mar. 2017, pp. 3-12.
Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13, Sep. 2018, pp. 3528-3538.
Mileo A.M. et al., "Polyphenols: Immunomodulatory and Therapeutic Implication in Colorectal Cancer" *Frontiers in Immunology*, vol. Apr. 10, 2019, 10 pages.
Milko R. et al., "Survival of L. easel DG (CNCMI1572) in the gastrointestinal tract of a healthy paediatric population", *European Journal of Nutrition, Steinkopff Verlag*, vol. 58 No. 8, Nov. 2018, 10 pages.
Nanau R.M. et al., "Nutritional and Probiotic Supplementation in Colitis Models" *Digestive Diseases and Sciences, Kluwer Academic Publishers-Plenum Publishers*, vol. 57 No. 11, Jun. 2012, pp. 2786-2810.
Non-Final Office Action for U.S. Appl. No. 17/090,669 filed Nov. 5, 2020, on behalf of Sofar S.P.A. dated Feb. 17, 2022. 45 Pages.
Notice of Allowance for U.S. Appl. No. 16/301,361, filed Nov. 13, 2018, on behalf of Sofar S.P.A. dated Mar. 30, 2022. 11 Pages.
Rajendran V.M. et al., "Na-H Exchanger Isoform-2 (NHE2) Mediates Butyrate-dependent Na+ Absorption in Dextran Sulfate Sodium (DSS)-induced Colitis" *Journal of Biological Chemistry*, vol. 290 No. 42, Oct. 2015, 10 pages.
Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" *Biomed Research International*, vol. 2015, Jan. 2015, pp. 1-15.
Xu J. et al., "Intake of blueberry fermented by *lactobacillus plantarum* affects the guy microbiota of L-name treated rats" *Evidence-Based Complementary and Alternative Medicine*, vol. 2013, Jan. 2013, pp. 1-9.
Xue H. Lactose-Induced Chronic Diarrhea Results from Abnormal Luminal Microbial Fermentation and Disorder of Ion Transport in the Colon *Frontiers in Physiology*, vol. 11, Jul. 2020, pp. 1-14.
Yehua Y. "Mixed fermentation of blueberry pomace with *L. rhamnosus GG* and ingredient, antioxidant activity and health-promoting benefits", *Food and Chemical Toxicology*, vol. 131, 2019, 8 pages.
Yoshida Y. et al., "Oral administration of *Lactobacillus plantarum Lq80* and *Megasphaera elsdenii iNP-001* induces efficient recovery

(56) References Cited

OTHER PUBLICATIONS from mucosal atrophy in the small and the large intestines of weaning piglets" *Animal Science Journal*, vol. 80, 2009, pp. 709-715.

\* cited by examiner

TOPICAL COMPOSITION FOR USE IN THE TREATMENT OF INFLAMMATORY BOWEL DISEASE

RELATED APPLICATIONS

This application is a 35 U.S.C. 371 national stage filing from International Application No. PCT/IB2015/052938, filed Apr. 22, 2015, which claims priority to Italian Application No. MI2014A000751, filed Apr. 23, 2014, the teachings of which are incorporated herein by reference.

The present invention relates to a topical composition containing a probiotic and hyaluronic acid or a pharmaceutically acceptable salt thereof, for use in the treatment and/or prevention of inflammatory bowel disease.

STATE OF THE ART

Inflammatory bowel disease ("IBD") is characterized by chronic inflammation of the intestinal wall and includes inter alia Crohn's disease and ulcerative colitis.

Conventional therapies are represented mainly by: 5-aminosalicylic acid (5-ASA), corticosteroids, azathioprine/6-mercaptopurine, methotrexate, cyclosporine, and anti-TNFα agents, which are mainly intended to modulate the immune system [1].

These diseases are "idiopathic" diseases, i.e. with unknown cause. The predominant pathogenetic hypothesis is that of an abnormal intestine immunological reaction against antigens (for example, bacteria normally present in the intestine). This immunological imbalance can be established due to an altered interaction between genetic factors of the individual and the environmental factors.

On the other hand, probiotics, defined as "live microorganisms which when administered in adequate amounts confer a health benefit on the host" [2] could modulate in a positive way the human microbiota, i.e. the set of symbiotic microorganisms which are found in the digestive tract, allowing to increase the commensal bacteria at the expense of the pathogen ones present in greater quantities in patients with IBD.

Their mechanism of action is not yet clear, but it can be assumed that probiotics modulate the intestinal permeability and the mucosal immune system, keeping the pathogenic bacteria away from the surface of the intestinal mucosa [1, 3].

Several strains were used in IBD and a number of publications attest their efficacy [4].

However, to date only few clinical studies have been published relating to the administration of probiotics in the form of a rectal preparation, and only in combination with conventional therapies [5-8].

In particular, the publication Dig. Dis. Sci. 2011, 56:1178-1187 [5] demonstrated that the administration of 5-ASA orally alone or together with *Lactobacillus casei* DG orally has no significant effect on the gut flora, unlike the combined administration of 5-ASA orally and of said *Lactobacillus* rectally.

This work highlighted a significant topical and anti-inflammatory activity of the probiotic, when used in conjunction with conventional therapies.

A possible mechanism of action of the association 5-ASA and *Lactobacillus casei* DG rectally may be related to alterations in the microbial flora that adheres to the mucosa, thus contributing to the manipulation of the mucosal immune response and changing the balance of pro-inflammatory cytokines in favor of the anti-inflammatory ones.

However, the above clinical trials do not discuss the fundamental aspect of the "mucosal healing" in the treatment of inflammatory bowel diseases, that is the complete absence of any inflammatory and ulcerative lesions. In clinical practice, the "mucosal healing" is associated with long term symptomatic remission, and a longer interval without recurrence. This results in a reduction in the frequency of hospitalizations, complications and surgical resections, with a significant improvement of the quality of life of the patient [9, 10].

Hyaluronic acid, a glycosaminoglycan, is known to play an important role in ensuring the hydration of the tissues, at the same time protecting them from excessive stresses and strains [11-13].

By stimulating the formation of collagen and connective tissue, hyaluronic acid protects the body from viruses and bacteria, increases the plasticity of tissues and ensures optimal skin hydration [11, 14].

In the absence of formulations capable of dealing with both the treatment of inflammatory bowel diseases and the appearance of the "mucosal healing", the need for an alternative formulation to respond effectively to these challenges is therefore felt.

DESCRIPTION

It has now surprisingly been found that a topical composition containing a probiotic and hyaluronic acid is particularly advantageous in the treatment of inflammatory bowel disease. In particular, in the abovementioned composition, the probiotic and hyaluronic acid show a surprising synergistic effect in the treatment of the abovementioned disease.

Therefore, the object of the present invention is a topical composition containing a probiotic and hyaluronic acid or a pharmaceutically acceptable salt thereof, and preferably at least one physiologically acceptable excipient, for use in the treatment of inflammatory bowel disease, such as Crohn's disease and ulcerative colitis.

A probiotic according to the invention is selected from *Lactobacillus acidophilus, Lactobacillus brevis, Lactobacillus buchneri, Lactobacillus casei, Lactobacillus paracasei, Lactobacillus catengforme, Lactobacillus cellobiosus, Lactobacillus crispatus, Lactobacillus curvatus, Lactobacillus delbrueckii, Lactobacillus fermentum, Lactobacillus jensenii, Lactobacillus leichmannii, Lactobacillus minutus, Lactobacillus plantarum, Lactobacillus reuteri, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infants, Bifidobacterium longum, Bifidobacterium plantarum, Bifidobacterium pseudocatenulatum, Bifidobacterium pseudolongum, Streptococcus lactis, Streptococcus raffinolactis, Streptococcus thermophilus*, or a mixture thereof.

Preferably, the probiotic is a *Lactobacillus*, more preferably is *Lactobacillus casei*, even more preferably is *Lactobacillus casei* DG (strain deposited at the Pasteur Institute in Paris with the deposit number I-1572CNCM).

Hyaluronic acid or a pharmaceutically acceptable salt thereof according to the invention is a high molecular weight hyaluronic acid, it preferably has a molecular weight comprised between 500,000 and 3,000,000 dalton, more preferably greater than or equal to 1,000,000 dalton.

Physiologically acceptable excipients according to the present invention are those known to the expert in the field, as described in the *Handbook of Pharmaceutical Excipients, sixth edition* 2009, incorporated herein by reference.

Examples of particularly preferred excipients according to the present invention include, but are not limited to, diluents, binders, surfactants, gelling agents, stabilizers.

A particularly preferred excipient according to the present invention is xanthan gum.

According to the invention, the composition contains an amount of living probiotic cells of between 200 million and 10 billion, preferably between 500 million and 2 billion.

According to one embodiment of the invention, the composition contains an amount of living probiotic cells comprised between 0.1 and 3% by weight, preferably less than 1% by weight, with respect to the total weight of the composition.

According to the invention, the composition contains an amount of hyaluronic acid or a pharmaceutically acceptable salt thereof comprised between 10 mg and 300 mg, preferably between 50 mg and 150 mg.

According to one embodiment of the invention, the composition contains an amount of hyaluronic acid or a pharmaceutically acceptable salt thereof comprised between 3 and 15% by weight, preferably of about 5% by weight, with respect to the total weight of the composition.

According to a particularly preferred embodiment of the invention, the composition contains an amount of living probiotic cells of between 0.1 and 3%, and an amount of hyaluronic acid of between 3 and 15% of the total weight of the composition.

According to the present invention, the composition may be administered orally or rectally, preferably it is administered rectally.

The composition of the present invention acts mainly at a topical level, i.e. it does not enter the circulatory system but exerts its action only at a local level through a combination of bacterial load reduction at the application site, and repair of the intestinal mucosa.

In fact, the probiotic and hyaluronic acid act in synergy on the inflammatory process at the intestinal level, reducing the pro-inflammatory factors and increasing the anti-inflammatory ones.

The probiotic modulates, directly or indirectly, the so-called "gut microbiata", exerting an important action on the intestinal permeability and the mucosal immune system; in this way, it allows to keep the potentially pathogenic bacteria, responsible for an excessive immune and inflammatory response, away from the surface of the intestinal mucosa.

Hyaluronic acid is, however, a compound with significant cicatricial and anti-inflammatory properties, by means of a direct action on TLR (Toll-Like Receptors). Furthermore, by stimulating the formation of collagen and connective tissue, it protects the body from viruses and bacteria, increases the plasticity of tissues and ensures optimal hydration of the skin. This protective action allows to preserve the integrity of the intestinal mucosa and to promote the so-called "mucosal healing".

When administered rectally, the composition of the invention can be formulated in semi-solid or liquid form, preferably as a cream, ointment, pomade, solution, suspension, powder to disperse in water or gel; more preferably, the composition is formulated as powder to disperse in water.

The previously mentioned components and excipients, preferably xanthan gum, used in the composition of the invention, provide a greater consistency and a higher viscosity to the preparation, necessary to ensure that the product may remain in situ for a longer time.

According to a preferred embodiment, the composition of the invention is administered in the form of an enema or a rectal foam, preferably in the form of an enema.

Therefore, thanks to the synergic effect of the probiotic and hyaluronic acid, the composition of the invention acts directly on the ongoing inflammatory process, by significantly stimulating the production of collagen and connective tissue, resulting in the repair of the intestinal mucosa injured by the onset of inflammatory bowel disease.

Furthermore, the composition of the invention is able to play an important immunomodulatory role in the modification of the composition of the human microbiota, by increasing the commensal species and reducing the presence of potentially pathogenic species.

According to an embodiment of the present invention, the composition may be administered alone or in combination with a traditional inflammatory bowel disease therapeutic agent selected from 5-ASA, corticosteroids, azathioprine/6-mercaptopurine, methotrexate, cyclosporine, and anti-TNFα agents.

Preferably, the composition is administered rectally, one or more times per day, more preferably twice a day.

The composition of the invention is administered for a period of treatment comprised between 2 and 16 weeks, preferably for a period comprised between 4 and 12 weeks, even more preferably for a period of at least 8 weeks.

According to a further embodiment of the present invention, the composition is administered as a combined preparation with one of the abovementioned conventional therapeutic agents, for simultaneous, separate or sequential use.

A further object of the present invention is the composition containing a probiotic and hyaluronic acid or a pharmaceutically acceptable salt thereof, and preferably at least one physiologically acceptable excipient, for use in the prevention of acute radiation proctitis.

Such use is particularly directed to patients undergoing radiation therapy for prostate cancer.

EXPERIMENTAL PART

The object of the present invention is a topical composition containing a probiotic and hyaluronic acid or a pharmaceutically acceptable salt thereof, and preferably, at least one physiologically acceptable excipient.

This formulation will be the object of a clinical study aimed to verify its effectiveness in the treatment of inflammatory bowel disease, such as Crohn's disease and ulcerative colitis.

The following table summarizes the qualitative and quantitative composition of the above invention:

| RAW MATERIAL | mg/sachet | % |
|---|---|---|
| Sorbitol | 1825 | 83 |
| Xanthan gum | 250 | 11.5 |
| Sodium hyaluronate | 100 | 4.5 |
| *Lactobacillus casei* DG | 5 | 1 |

Before achieving such a formulation, some tests were carried out with the aim of obtaining a product with the most appropriate composition for the treatment of inflammatory bowel disease, and with chemical-physical characteristics optimal for a rectal preparation.

Some possible modifications in the formulation of the composition object of this invention are reported below.

Considering that the final solution, which is to be administered rectally, must be an isosmotic solution, it is necessary to modify in an appropriate manner the qualitative and quantitative composition of the thixotropic agents. In this respect, it is important to consider that also the hyaluronic acid possess a viscosifying power of, and it is, therefore, necessary to dose in an appropriate manner the quantities of excipients which have a similar power.

The amount of hyaluronic acid may be increased up to a quantity equal to about 200-300 mg, corresponding to about 9-14% with respect to the total weight of the composition, thereby reducing the xanthan gum, in order to avoid too viscous formulations which would lead to the possible formation of lumps.

Otherwise, the percentage of hyaluronic acid may be left unchanged and the amount of xanthan gum increased by about 0.5-6%.

The xanthan gum may also optionally be replaced by another viscosifying agent, such as hydroxypropylmethylcellulose (HPMC), which has a viscosity power greater than xanthan gum. Such an excipient, however, having also a greater tendency to form lumps, could be increased only up to a 3-4%, compared to what was instead done with xanthan gum.

Finally, the amount of living lactobacilli cells could be increased even up to about 10 billion, corresponding to approximately 2% of the total weight of the composition (or, taking into account the excess of living cells which is normally employed, up to a maximum of 9%), without minimally perturbing the final composition, especially in terms of viscosity As a result, the following compositions may be obtained:

| RAW MATERIAL | mg/sachet | % |
|---|---|---|
| Sorbitol | 1826 | 83 |
| Xanthan gum | 252 | 12 |
| Sodium hyaluronate | 100 | 4.5 |
| Lactobacillus casei DG | 5 (1 billion) | 0.5 |

| RAW MATERIAL | mg/sachet | % |
|---|---|---|
| Sorbitol | 1716 | 78 |
| Xantban gum | 374 | 17 |
| Sodium hyaluronate | 100 | 4.5 |
| Lactobacillus casei DG | 5 (1 billion) | 0.5 |

| RAW MATERIAL | mg/sachet | % |
|---|---|---|
| Sorbitol | 1683 | 76.5 |
| Xanthan gum | 200 | 9 |
| Sodium hyaluronate | 300 | 14 |
| Lactobacillus casei DG | 5 (1 billion) | 0.5 |

| RAW MATERIAL | mg/sachet | % |
|---|---|---|
| Sorbitol | 1892 | 86 |
| HPMC | 200 | 9 |
| Sodium hyaluronate | 100 | 4.5 |
| Lactobacillus casei DG | 5 (1 billion) | 0.5 |

| RAW MATERIAL | mg/sachet | % |
|---|---|---|
| Sorbitol | 1727 | 78.5 |
| HPMC | 155 | 7 |
| Sodium hyaluronate | 300 | 14 |
| Lactobacillus casei DG | 5 (1 billion) | 0.5 |

| RAW MATERIAL | mg/sachet | % |
|---|---|---|
| Sorbitol | 1826 | 83 |
| HPMC | 260 | 12 |
| Sodium hyaluronate | 100 | 4.5 |
| Lactobacillus casei DG | 5 (1 billion) | 0.5 |

| RAW MATERIAL | Mg/Bst | % |
|---|---|---|
| Sorbitol | 1650 | 75 |
| Xanthan gum | 200 | 9 |
| Sodium hyaluronate | 300 | 14 |
| Lactobacillus casei DG | 50 (10 billion) | 2 |

These are only formulation examples aimed at showing the possible combinations of the various components of the above composition.

REFERENCES

1. Scaldaferri F. et al. "Gut microbial flora, prebiotics and probiotics in IBD: their current usage and utility", *BioMed Research International* 2013, 9 pages.
2. Food and Agriculture Organization. Health and nutritional properties of probiotics in food including powder milk with live lactic acid bacteria. October 2001: 34 pages.
3. Martin R. et al. "Role of commensal and probiotic bacteria in human health: a focus on inflammatory bowel disease", *Microbial Cell Factories* 2013, 12: 71.
4. Floch M. H. et al. "Recommendations for probiotic use 2011 Update", *J. Clin. Gastroenterol.* 2011, 45: S168-S171.
5. D'Incà R. et al. "Rectal administration of *Lactobacillus casei* DG modifies flora composition and Toll-Like receptor expression in colonic mucosa of patients with mild ulcerative colitis", *Dig. Dis. Sci.* 2011, 56: 1178-1187.
6. De Souza M. M. et al. "Effects of budesonide and probiotics enemas on the systemic inflammatory response of rats with experimental colitis", *Acta Cirùrgica Brasileira* 2007, 22 (Suppl. 1): 40-45.
7. Matthes H. et al. "Clinical trial: probiotic treatment of acute distal ulcerative colitis with rectally administered Escherichia Coli Nissle 1917 (EcN)", *BMC Complementary and Alternative Medicine* 2010, 10: 13.
8. Oliva S. et al. "Randomised clinical trial: the effectiveness of *Lactobacillus Reuteri* ATCC 55730 rectal enema in children with active distal ulcerative colitis", *Aliment. Pharmacol. Ther.* 2012, 35: 327-334.
9. Orlando A. et al. "Clinical implications of mucosal healing in the management of patients with inflammatory bowel disease", *Digestive and Liver Disease* 2013, 45, 986-991.
10. Mazzuoli S. et al. "Definition and evaluation of mucosal healing in clinical practice", *Digestive and Liver Disease* 2013, 45, 969-977.
11. Collins M. N. and Birkinshaw C. "Hyaluronic acid based scaffolds for tissue engineering A review", *Carbohydrate Polymers* 2013, 1262-1279.

12. Necas J. et al. "Hyaluronic acid (hyaluronan): a review", *Veterinarni Medicina* 2008, 53(8): 397-411.
13. Fakhari A. and Berkland C. "Applications and emerging trends of hyaluronic acid in tissue engineering, as a dermal filler and in osteoarthritis treatment", *Acta Biomaterialia* 2013, 9, 7081-7092.
14. Price R. D. et al. "Hyaluronic acid: the scientific and clinical evidence", *Journal of Plastic, Reconstructive & Aesthetic Surgety* 2007, 60: 1110-1119.

The invention claimed is:

1. A composition comprising a probiotic and hyaluronic acid or a pharmaceutically acceptable salt thereof, wherein the composition is a rectally administered topical composition comprising the probiotic and the hyaluronic acid in an effective amount for treating inflammatory bowel disease, and wherein the hyaluronic acid has a molecular weight ranging from 500,000 to 3,000,000 dalton.

2. The composition of claim 1 further comprising at least one physiologically acceptable excipient.

3. The composition of claim 1 wherein the probiotic is selected from the group consisting of *Lactobacillus acidophilus, Lactobacillus brevis, Lactobacillus buchneri, Lactobacillus casei, Lactobacillus paracasei, Lactobacillus catenaforme, Lactobacillus cellobiosus, Lactobacillus crispatus, Lactobacillus curvatus, Lactobacillus delbrueckii, Lactobacillus fennentum, Lactobacillus jensenii, Lactobacillus leichmannii, Lactobacillus minutus, Lactobacillus plantarum, Lactobacillus reuteri, Lactobacillus rogosae, Lactobacillus salivarius, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infants, Bifidobacterium longum, Bifidobacterium plantarum, Bifidobacterium pseudocatenulatum, Bifidobacterium pseudolongum, Streptococcus lactis, Streptococcus raffinolactis, Streptococcus thermophilus*, and mixtures thereof.

4. The composition of claim 1 wherein the probiotic is a *Lactobacillus*.

5. The composition of claim 4 wherein the probiotic is *Lactobacillus casei*.

6. The composition of claim 1 wherein the probiotic comprises living probiotic cells present in an amount ranging from 200 million to 3 billion.

7. The composition of claim 6 wherein the living probiotic cells are present in an amount ranging from 500 million to 2 billion.

8. The composition of claim 1 wherein the probiotic comprises living probiotic cells present in an amount ranging from 0.1% to 3% by weight with respect to the total weight of the composition.

9. The composition of claim 8 wherein the living probiotic cells are present in an amount of less than 1% by weight of the total weight of the composition.

10. The composition of claim 1 wherein the hyaluronic acid has a molecular weight ranging from 1,000,000 to 3,000,000 dalton.

11. The composition of claim 1 wherein the hyaluronic acid or the pharmaceutically acceptable salt thereof is present in an amount ranging from 3% to 15% by weight of the total weight of the composition.

12. The composition of claim 11 wherein the hyaluronic acid or the pharmaceutically acceptable salt thereof is present in an amount of about 5% by weight of the total weight of the composition.

13. The composition of claim 1 wherein the hyaluronic acid or the pharmaceutically acceptable salt thereof is present in an amount ranging from 10 mg to 300 mg.

14. The composition of claim 13 wherein the hyaluronic acid or the pharmaceutically acceptable salt thereof is present in an amount ranging from 50 mg to 150 mg.

15. The composition of claim 1 wherein the probiotic comprises living probiotic cells present in an amount ranging from 0.1% to 3% by weight with respect to the total weight of the composition, and wherein the hyaluronic acid is present in an amount ranging from between 3% to 15% by weight with respect to the total weight of the composition.

16. The composition of claim 1 wherein the composition is in the form of a cream, an ointment, a pomade, a solution, a suspension, a water dispersible powder or a gel dispersible powder.

17. The composition of claim 16 wherein the composition is in the form of a gel dispersible powder.

18. The composition of claim 1 further comprising a traditional inflammatory bowel disease composition selected from the group consisting of 5-ASA, corticosteroid, azathioprine/6-mercaptopurine, methotrexate, cyclosporine, and an anti-TNFα agent.

19. A method of treating inflammatory bowel disease comprising rectally administering the composition according to claim 1 to a patient in need thereof.

20. The method of claim 19 wherein the inflammatory bowel disease is Crohn's disease.

21. The method of claim 19 wherein the inflammatory bowel disease is ulcerative colitis.

22. The method of claim 19 wherein the composition is in the form of a cream, an ointment, a pomade, a solution, a suspension, a water dispersible powder or a gel dispersible powder.

23. The method of claim 22 wherein the composition is in the form of a gel dispersible powder.

24. The method of claim 19 comprising rectally administering the composition in combination with administering a traditional inflammatory bowel disease composition selected from the group consisting of 5-ASA, corticosteroid, azathioprine/6-mercaptopurine, methotrexate, cyclosporine, and an anti-TNFα agent.

25. The method of claim 24 wherein the composition is administered simultaneously with, separately from, or sequentially with the administration of the traditional inflammatory bowel disease composition.

26. The composition of claim 1, wherein the probiotic is a *Lactobacillus casei* DG deposited at the Pasteur Institute in Paris with the deposit number I-1572CNCM.

* * * * *